United States Patent [19]

Mitchell et al.

[11] 4,101,596
[45] Jul. 18, 1978

[54] LOW PRESSURE XYLENE ISOMERIZATION

[75] Inventors: Kenneth M. Mitchell, Mount Laurel, N.J.; John J. Wise, Media, Pa.

[73] Assignee: Mobil Oil Company, New York, N.Y.

[21] Appl. No.: 758,214

[22] Filed: Jan. 10, 1977

[51] Int. Cl.$^2$ .............................................. C07C 15/08
[52] U.S. Cl. .......................... 260/668 A; 208/DIG. 2
[58] Field of Search ..................................... 260/668 A

[56] References Cited

U.S. PATENT DOCUMENTS

| 3,790,471 | 2/1974 | Arganer et al. | 260/668 A |
| 3,856,873 | 12/1974 | Burress | 260/668 A |
| 4,007,231 | 2/1977 | Butter | 260/668 A |

*Primary Examiner*—Veronica O'Keefe
*Attorney, Agent, or Firm*—Charles A. Huggett; Michael G. Gilman; Raymond W. Barclay

[57] ABSTRACT

Long on-stream periods of low pressure, vapor phase isomerization of xylenes is achieved in a system having tolerance of ethyl benzene in the charge by using a zeolite catalyst such as zeolite ZSM-5 at partial pressure of eight carbon atom aromatics below 100 pounds per square inch and temperature of 500° F. to 800° F.

8 Claims, 1 Drawing Figure

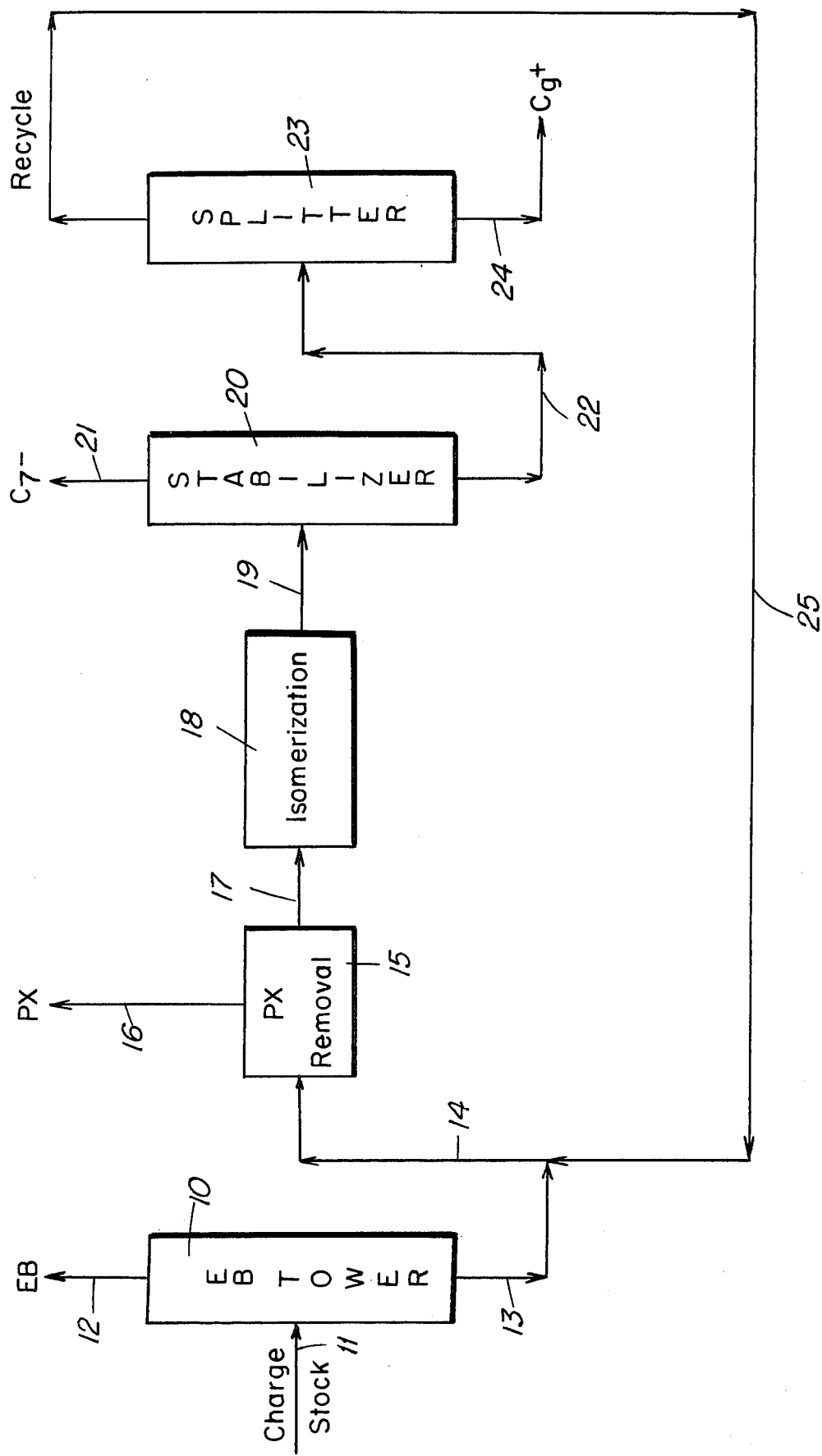

LOW PRESSURE XYLENE ISOMERIZATION

BACKGROUND OF THE INVENTION

Since the announcement of the first commercial installation of Octafining in Japan in June, 1958, this process has been widely installed for the supply of p-xylene. See "Advances in Petroleum Chemistry and Refining" volume 4 page 433 (Interscience Publishers, New York 1061). That demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point° F. | Boiling Point° F. | Density Lbs./U.S. Gal. |
|---|---|---|---|
| Ethyl benzene | −139.0 | 277.0 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources are catalytically reformed nahthas and pyrolysis distillates. The $C_8$ aromatic fractions from these sources vary quite widely in composition but will usually be in the range 10 to 32 wt. % ethyl benzene with the balance, xylenes, being divided approximately 50 wt. % meta, and 25 wt. % each of para and ortho.

In turn, calculated thermodynamic equilibra for the $C_8$ aromatic isomers at Octafining conditions are:

| Temperature | 850° F. |
|---|---|
| Wt. % Ethyl benzene | 8.5 |
| Wt. % para xylene | 22.0 |
| Wt. % meta xylene | 48.0 |
| Wt. % ortho xylene | 21.5 |
| TOTAL | 100.0 |

An increase in temperature of 50° F. will increase the equilibrium concentration of ethyl benzene by about 1 wt. %, ortho-xylene is not changed and para and meta xylenes are both decreased by about 0.5 wt. %.

Individual isomer products may be separated from the naturally occurring mixtures by appropriate physical methods. Ethyl benzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes.

Octafining process operates in conjunction with the product xylene or xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

The isomerizer unit itself is most simply described as a single reactor catalytic reformer. As in reforming, the catalyst contains a small amount of platinum and the reaction is carried out in a hydrogen atmosphere.

Octafiner unit designs recommended by licensors of Octafining usually lie within these specification ranges:

| Process Conditions | |
|---|---|
| Reactor Pressure | 175 to 225 PSIG |
| Reactor Inlet Temperature Range | 830–900° F. |
| Heat of Reaction | Nil |
| Liquid Hourly Space Velocity | 0.6 to 1.6 Vol/Vol/Hr. |
| Number of Reactors, Downflow | 1 |
| Catalyst Bed Depth, Feet | 11 to 15 |
| Catalyst Density, Lb/Cu. Ft. | 38 |
| Recycle Circulation, Mols Hydrogen/ Mol Hydrocarbon Feed | 7.0 to 14.0 |
| Maximum Catalyst Pressure Drop, PSI | 20 |

It will be apparent that under recommended design conditions, a considerable volume of hydrogen is introduced with the $C_8$ aromatics. In order to increase throughput, there is great incentive to reduce hydrogen circulation with consequent increase in aging rate of the catalyst. Aging of catalyst occurs through deposition of carbonaceous materials on the catalyst with need to regenerate by burning off the coke when the activity of the catalyst has decreased to an undesirable level. Typically the recommended design operation will be started up at about 850° F. with reaction temperature being increased as needed to maintain desired level of isomerization until reaction temperature reaches about 900° F. At that point the isomerizer is taken off stream and regenerated by burning of the coke deposit.

Actual operation of Octafining varies from the recommended ideal in some cases. In the case of one commercial Octafiner, temperature has been reduced for increased throughput such that a cycle is begun at 760° F. and ended at 860° F. Concurrently, hydrogen recycle is reduced to 6.5 mols of $H_2$ per mol of hydrocarbon charge. Cycle time between regenerations is cut to 3 months at these conditions.

During regeneration, burning proceeds very slowly with diluted oxidizer medium in order to minimize damage to the catalyst. The several days required for regeneration are non-productive and the catalyst after regeneration is at a reduced activity level. For example, an operation at a hydrogen to hydrocarbon recycle ratio of 6.5 results in a cycle life of about 3 months between regenerations with replacement of the catalyst required after about 1 year, four cycles.

In a typical plant for utilization of Octafining, a mixture of $C_8$ aromatics is introduced to an ethyl benzene tower wherein the stream is stripped of a portion of its ethyl benzene content, to an extent consistent with retaining all the xylenes in the feed stream without unduly expensive "superfractionation." Ethyl benzene is taken overhead while a bottom stream, consisting principally of xylenes, together with a significant amount of ethyl benzene, passes to a xylene splitter column. The bottoms from the xylene splitter constituted by o-xylene and $C_9$ aromatics passes to the o-xylene tower from which o-xylene is taken overhead and heavy ends are removed. The overhead from the xylene splitter column is transferred to conventional crystallization separation.

The crystallizer operates in the manner described in Machell et al., U.S. Pat. No. 3,662,013 dated May 9, 1972.

Because it's melting point is much higher than that of the other $C_8$ aromatics, p-xylene is readily separated in the crystallizer after refrigeration of the stream and a xylene mixture lean in p-xylene is transferred to an isomerization unit. The isomerization charge passes through a heater, is admixed with hydrogen and the mixture is introduced to the isomerizer.

Isomerized product from the isomerizer is cooled and passed to a high pressure separator from which separated hydrogen can be recycled in the process. The liquid product of the isomerization passes to a stripper from which light ends are passed overhead. The remaining liquid product constituted by $C_8+$ hydrocarbons is recycled in the system to the inlet of the xylene splitter.

It will be seen that the system is adapted to produce maximum quantities of p-xylene from a mixed $C_8$ aromatic feed containing all of the xylene isomers plus ethyl benzene. The key to efficient operation for that purpose is in the isomerizer which takes crystallizer effluent lean in p-xylene and converts the other xylene isomers in part to p-xylene for further recovery at the crystallizer.

Among the xylene isomerization processes available in the art, Octafining has been unique in its ability to convert ethyl benzene. Other xylene isomerization processes have required extremely expensive fractionation to separate that component of $C_8$ aromatic fractions. As will be seen from the table of properties above, the boiling point of ethyl benzene is very close to those of p- and m-xylene. Complete removal of ethyl benzene from the charge is impractical. The usual expedient for coping with the problem is an ethyl benzene separation column in the isomerizer-separator loop when using catalyst other than those characteristic of Octafining. It will be seen that Octafining does not need this expensive auxiliary to prevent build up of ethyl benzene in the loop. This advantageous feature is possible because the Octafining catalyst converts ethyl benzene.

The Octafining process has been extensively discussed in the literature, for example:

1. Pitts, P. M., Connor, J. E., Leun, L. N., Ind. Eng. Chem., 47, 770 (1955).
2. Fowle, M. J., Bent, R. D., Milner, B. E., presented at the Fourth World Petroleum Congress, Rome, Italy, June 1955.
3. Ciapetta, F. G., U.S. Pat. No. 2,550,531 (1951).
4. Ciapetta, F. G., and Buck, W. H., U.S. Pat. No. 2,589,189.
5. Octafining Process, Process Issue, Petroleum Refinery, 1st Vol. 38 (1959), No. 11, Nov., p. 278.

A typical charge to the isomerizing reactor (effluent of the crystallizer) may contain 17 wt. % ethyl benzene, 65 wt. % m-xylene, 11 wt. % p-xylene and 7 wt. % o-xylene. The thermodynamic equilibrium varies slightly with temperature. The objective in the isomerization reactor is to bring the charge as near to theoretical equilibrium concentrations as may be feasible consistent with reaction times which do not give extensive cracking and disproportionation.

Ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethane and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has put a very small effect on ethyl benzene approach to equilibrium.

Concurrent loss of ethyl benzene to other molecular weight products relates to % approach to equilibrium. Products formed from ethyl benzene include $C_6+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecular weight products varies with contact time. By-products include naphthenes, benzene, toluene, $C_9+$ aromatics and $C_5$ and lighter hydrocracking products.

Ethyl benzene has been found responsible for a relatively rapid decline in catalyst activity and this effect is proportional to its concentration in a $C_8$ aromatic feed mixture. It has been possible then to relate catalyst stability (or loss in activity) to feed composition (ethyl benzene content and hydrogen recycle ratio) so that for any $C_8$ aromatic feed, desired xylene products can be made with a selected suitably long catalyst use cycle.

Another xylene isomerization which has achieved widespread commercial use is low pressure operation in vapor phase. Temperatures employed are in the same range as for Octafining, in the neighborhood of 850° F. Pressures are only that required to equal pressure drop through the downstream recovery towers, heat exchanges and the like. For all practical purposes, this is an atmospheric pressure reaction with reactor inlet pressure of about 30 pounds per square inch, gauge. The catalyst is essentially silica-alumina, the acid amorphous heterogeneous catalyst employed in a number of such acid catalyzed processes. Several advantages for that type of isomerization will be immediately apparent.

The unit cost of catalyst is drastically reduced by ommission of platinum. At these low pressures, the reactor vessels are made of inexpensive steel and need no structural provision for resisting pressure stress. The process is practical without introduction of molecular hydrogen and needs no auxiliaries for manufacture and recycle of that gas. These features greatly reduce capital and operating costs and have made the low pressure process essentially competitive with Octafining despite the requirement for large vessels at low pressure and low space velocity and the operating disadvantages inherent in the process.

A primary drawback of low pressure vapor phase isomerization as practiced heretofore is its low tolerance for ethyl benzene in the charge. The catalyst will convert ethyl benzene only at high severities such that unacceptable loss of xylene occurs by disproportionation.

Low pressure isomerization as practiced heretofore accepts a further disadvantage in that the catalyst rapidly declines in activity due to deposition of "coke," a carbonaceous layer masking the active sites of the porous silica-alumina catalyst presently conventional in this operation. The coke can be removed by burning with air to regenerate the activity of the catalyst. Continuity of operation is achieved by the well-known "swing reactor" technique employing two or more reactors, one of which is on stream while burning regeneration is conducted on a reactor containing spent catalyst which has lost activity by coke deposition. Cycles of two to four days are common practice using one reactor on stream for that period and then shifting to a freshly regenerated vessel.

Present commercial practice involves many large plants of both the Octafining and low pressure types in a loop of p-xylene separation and recycle of other isomers, together with such quantity of ethyl benzene as may be present, through isomerization and back to p-xylene recovery. The commercial options presently in use are Octafining at high pressure with large quantities of hydrogen or low pressure (essentially atmospheric) isomerization with complicated cycling of a swing reactor and necessity for expensive distillation to remove ethyl benzene from the charge to some acceptable level, usually about 5%.

A further alternative heretofore described is isomerization in liquid phase at a pressure adequate to maintain that phase. Highly active zeolite catalysts are effective under these conditions and demonstrate long cycle life, possibly because precursors of coke are dissolved by the reactant liquid and flushed from the reactor before deterioration to coke. See, for example, Wise, U.S. Pat. No. 3,377,400; Bowes et al., U.S. Pat. No. 3,578,723; and Haag et al., U.S. Pat. No. 3,856,871.

It is further known that zeolite ZSM-5 is a very effective catalyst for isomerization of xylenes. See Argauer et al., U.S. Pat. No. 3,790,471; Burress, U.S. Pat. No. 3,856,873; Morrison, U.S. Pat. No. 3,856,872; and Haag et al., supra. It should be noted that Burress describes a wide range of operating conditions and demonstrates effectiveness of the catalyst at (1) low temperature, high pressure and (2) high temperature, low pressure operation over zeolite ZSM-5. On this state of the art, zeolite ZSM-5 can be expected to function effectively in low pressure, vapor phase isomerization, and indeed it does. That zeolite and the related zeolites are defined hereinafter by silica/alumina ratio, constraint index and crystal density. Further, in the absence of hydrogen, these zeolites accumulate coke on stream in the manner to be expected from knowledge in the art to require short cycle times, when operating outside the bounds of limits now found essential to prolonged on-stream periods.

SUMMARY OF THE INVENTION

It has now been demonstrated that a mixture of eight carbon atom aromatics can be isomerized by zeolites such as ZSM-5 in vapor phase with long on-stream periods by charging a mixture of such aromatics essentially free of peroxides at reactor temperatures in the range of 500° to 800° F. and partial pressure of aromatic hydrocarbons below 75 pounds per square inch, gauge (psig). This operation is well suited to modernization of present equipment for low pressure vapor phase isomerization as discussed above by replacing the usual silica-alumina catalyst with a zeolite as herein defined and adapting process conditions to the replacement catalyst. The principal adaptation takes into account the long on-stream periods which can be achieved. Only a single reactor is appropriate to the replacement catalyst. Other reactors may be retired from service or used in parallel during the many months that the catalyst retains its effectiveness.

In accordance with usual practice, tanks for storage of alkyl aromatic fractions are blanketed by an inert gas, e.g. nitrogen such that peroxides do not develop. However, if these undesirable compounds have been formed by contact of the $C_8$ aromatics with air, the necessary lack of peroxides can be achieved by percolation through alumina. A preferred method for removal is distillation prior to contact with the isomerization catalyst of the invention. This may be prior to introduction of the aromatic charge to the recovery and isomerization loop. Alternatively, the charge may be introduced in the loop prior to distillation for removal of higher boiling ($C_9+$) compounds formed in the isomerizer. Because the process of this invention has capability for conversion of ethyl benzene, the preliminary distillation is preferably operated to leave substantial amounts of ethyl benzene in the charge at very substantial saving in distillation cost. In a preferred embodiment, the process is operated to maintain a concentration of ethyl benzene in the loop approximately equal to that in the charge since the new catalysts show the property of converting ethyl benzene by disproportionation with very minor disproportion of xylenes, enabling removal by the usual fractionation in the loop of ethyl benzene conversion products.

THE DRAWING

Suitable apparatus for practicing the invention is illustrated by the flow diagram in the single FIGURE of the drawing.

DESCRIPTION OF THE SPECIFIC EMBODIMENTS

In the flow diagram of the annexed drawing, the principal elements of a typical low pressure isomerization unit are shown. Now shown are the parallel isomerization reactors necessary for continuous operation with conventional silica-alumina catalyst since only one reactor is needed in practice of the present invention. For typical operation, the existing ethyl benzene tower 10 is controlled to remove only a small portion, or none, of the ethyl benzene content of charge stock which contains 19.0% ethyl benzene, 20.3% o-xylene, 41.3% m-xylene, 18.6% p-xylene and 0.8% $C_9$ and heavier aromatics, by weight.

That charge stock is supplied by charge line 11 to tower 10 at a rate of 100,000 pounds per hour. Overhead from tower 10 by line 12 is constituted primarily by ethyl benzene, about 15,700 pounds per hour. The bottoms from tower 10 by line 13 is 84,300 pounds per hour of mixed xylenes and ethyl benzene supplied to recycle line 14 of the loop. There the fresh feed is mingled with 454,600 pounds per hour of recycle product from isomerization and distillation steps presently to be described. The mixed stream of 538,900 pounds per hour passes by line 14 to p-xylene recovery unit 15, e.g. fractional crystallization, from which 78,000 pounds per hour of p-xylene is discharged by line 16 as the principal product of the process.

From recovery unit 15, a stream of 8 carbon atom aromatics stripped of p-xylene passes by line 17 as 460,900 pounds per hour of feed to isomerization 18. In the isomerizer 18, the feed from line 17 is contacted in vapor phase with the acid form of zeolite ZSM-5 (H-ZSM-5) at 500°–800° F. and a pressure of 25 psig, resulting in conversion of xylenes to equilibrium concentration of the three isomers and conversion of ethyl benzene in part to benzene and diethyl benzenes. The effluent of isomerizer 18 is transferred by line 19 to stabilizer 20 from which compounds lighter than eight carbon atoms are taken overhead by line 21 and a bottoms stream of 458,800 pounds per hour is transferred by line 22 to splitter 23 from which a heavy bottoms fraction of compounds containing nine or more carbon atoms is discharged by line 24.

The overhead from splitter 23 is constituted essentially of eight carbon atom aromatic compounds in which the xylenes are essentially in equilibrium proportions. That stream is transferred by recycle line 25 for admixture with the fresh feed from line 13 as described above.

When operated in the manner described herein, the isomerization catalyst will remain on stream without regeneration for months, up to a year or more. As will be shown in comparative examples below, higher partial pressure of aromatics results in rapid decline in activity of the catalyst such that its service approaches that of inexpensive silica-alumina catalyst. Similarly, the catalyst of this invention is effective for isomerization of xylenes at higher temperatures and in the presence of peroxides, but declines in activity and/or selectivity at rates which approach that of the less expensive silica-alumina.

The pressure of isomerization according to the present invention is measured as partial pressure of aromatic hydrocarbons which shall be less than 100 psig. As partial pressure of aromatic hydrocarbons is increased, cycle life of the catalyst tends to decrease. The charge to the isomerizer may be at greater total pressure, if desired, by adding inert diluents such as nitrogen, hydrogen and the like, but it is preferred to practice the invention with undiluted hydrocarbons at a pressure only sufficient to balance downstream pressure drop through the distillation train and auxiliaries, say 25 psig. As is well known in the art, such materials as toluene and alkyl aromatics higher than 8 carbon atoms can improve approach to equilibrium in the isomerizer and the invention contemplates such modification. If such reaction modifiers are included, their partial pressure should be included in setting preferred conditions.

The zeolite catalysts utilized herein are members of a novel class of zeolites exhibiting some unusual properties. The zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even though the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conductive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12: and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5; ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specific X-ray powder diffraction pattern.

In a preferred synthesized form, the zeolite has a formula, in terms of mole ratios of oxides and in the anhydrous state, as follows:

$$(0.4-2.5)R_2O : (0-0.6)M_2O : Al_2O_3 : xSiO_2$$

wherein R is an organic nitrogen-containing cation derived from a 2-hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33 Angstroms.

TABLE I

| d (A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO₂ | 0.05–0.5 | 0.07–0.49 |
| H₂O/OH− | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8 \, SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$$(0.4-2.5)R_2O : (0-0.6)M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33Angstroms. Close examination of some individual samples of ZSM-35 may show a very weak line at 11.3-11.5Angstroms. This very weak line, however, is determined not to be a significant line for ZSM-35.

TABLE II

| d (A) | I/Io |
|---|---|
| 9.6 ± 0.2 — | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |

TABLE II-continued

| d (A) | I/Io |
|---|---|
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount to time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, as prepared, are catalytically inactive. They may be activated by heating in an inert atmosphere at 1000° F. for 1 hour, for example, followed by base exchange with ammonium salts of those species of zeolite from which alkalimetal cations must be removed, followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment of chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolites component and inorganic oxide gel matrix may vary widely with the zeolite content ranging from between about 1 to about 99 percent by weight and more usually in the range of about 5 to about 80 percent by weight of the composite.

The flexibility in concentration of active zeolite in a zeolite plus inert matrix composite catalyst is of particular value in modernization of existing low pressure isomerization faciities by adapting them to use of the invention. Typically, present low pressure isomerizers operate a WHSV of unity. The present catalyst is preferably operated at WHSV of pounds of $C_8$ aromatics per pound of zeolite per hour in the neighborhood of 8, i.e. WHSV of 5 with respect to 65% HZSM-5 with 35% of alumina. It will be seen that a much smaller amount of catalyst is used on shifting from amorphous silica alumina to a catalyst such as ZSM-5. But reduction of catalyst volume by this factor of 5 can result in catalyst beds so thin that distribution of reactants through the bed is adversely affected. One method of correction to obtain reactor ratio of length to diameter (L/D) equal to at least 0.2 is insertion of a liner to confine the bed to smaller diameter. Alternatively, the bed may be suplemented by a layer of inert granules above the catalyst. A third alternative is to form the catalyst with a higher proportion of inert matrix, say 70% alumina, 30% HZSM-5.

By whatever expedient may be adopted, the WHSV calculated as alkyl aromatic feed with respect to active zeolite component of the catalyst should be in the approximate range of 3 to 13 pounds of feed per pound of zeolite component of the catalyst per hour.

The space velocity discussed above refers to weight of aromatics in feed. Similarly to the discussion of catalyst, the aromatic feed may be diluted with inert materials such as saturated lower alkanes, nitrogen, hydrogen or the likes as desired. In general, such dilution is undesirable, but if the charge be diluted, the space velocity is calculated on the weight of alkyl aromatics (primarily of 8 carbon atoms).

The catalyst consists essentially of the specified zeolites, more particularly the catalyst is substantially free of metals having significant hydrogenation/dehydrogenation activity such as nickel, platinum and the like. It is found that the presence of significant metal activity of this nature causes rapid aging of the catalyst.

In the context of this invention, aging of the catalyst is conveniently observed with respect to activity for conversion of ethyl benzene in feed to the isomerizer. That conversion results in production of benzene, $C_{9+}$ aromatics and light hydrocarbons, probably by disproportionation of ethyl benzene to benzene and di-ethyl benzene and by transalkylation with xylene to produce such by-products as methyl ethyl benzene. Although loss of xylene is found to be a function of ethyl benzene conversion, it is apparent that the catalysts of this invention are much more effective in inducing intermolecular alkyl group transfer (bi-molecular transalkylation) of ethyl benzene than like reaction of xylene.

It has been found convenient to control the operation to compensate for aging by raising the temperature over the course of a run to maintain conversion of ethyl benzene at a substantially constant value. Thus a run of several months uninterrupted operation may be initiated at 500°–550° F. with xylene isomerization of about 100% approach of equilibrium, very small loss of xylenes and conversion of ethyl benzene at a level to maintain that compound in recycled isomerizate at a concentration equal to that in the feed. As the catalyst ages, the temperature is raised to maintain ethyl benzene conversion constant. The isomerization of xylenes maintains the close approach to 100% of equilibrium values of xylenes and the low level of xylene conversion to other compounds. In general, it will be desirable to terminate the run as reaction temperature reaches a value in the neighborhood of 750° F. for regeneration of the catalyst.

Pressure for operation according to the invention will be maintained at less than 100 psig partial pressure of eight carbon atom aromatics, preferably less than 50 psig. The nearest approach to 1 atmosphere permitted by the equipment will generally be preferred.

For purposes of comparison, data are provided below on a run outside the scope of the invention but at conditions not far removed, namely isomerization at 200 psig with a catalyst which contains the H/D metal nickel. The catalyst was 65 wt % NiHZSM-5 in a matrix of 35 wt % alumina. The charge stock was constituted:

| | |
|---|---|
| Ethyl benzene (EB) | 17.2 wt % |
| p-xylene | 10.7 |
| m-xylene | 65.6 |
| o-xylene | 6.5 |
| | 100.0 |

It will be seen that the composition represents a mixture from which some p- and o-xylene has been removed. Reaction conditions, with space velocity calculated with respect to composite catalyst pellets, are reported in Table 1 together with results of reaction.

TABLE 1

| Temp, ° F. | 649 | 649 | 649 | 649 | 649 |
|---|---|---|---|---|---|
| Pressure, PSIG | 203 | 205 | 205 | 205 | 205 |
| WHSV | 12 | 12 | 12 | 12 | 12 |
| $H_2$/HC | 0 | 0 | 0 | 0 | 0 |
| Material Balance | 98.7 | 99.4 | 100.4 | 100.4 | 99.5 |
| Time on Stream, Hrs. | 66.5 | 138.8 | 162.8 | 258.8 | 282.8 |
| Product Distribution, Wt. % | | | | | |
| $C_1$-$C_5$ | Trace | Trace | Trace | | |
| Benzene | 1.4 | 1.0 | 0.8 | 0.5 | 0.4 |
| Toluene | 0.7 | 0.4 | 0.3 | 0.2 | 0.1 |
| EB | 13.0 | 13.5 | 14.5 | 15.6 | 15.7 |
| P-xylene | 19.8 | 20.5 | 20.4 | 19.4 | 19.3 |
| O-xylene | 15.9 | 14.6 | 14.3 | 11.6 | 10.7 |
| M-xylene | 46.6 | 48.0 | 48.1 | 51.7 | 50.9 |
| $C_9$ Aromatics | 0.4 | 0.3 | 0.2 | 0.1 | 0.1 |
| $C_{10}$ Aromatics | 2.1 | 1.6 | 1.5 | 0.8 | 0.9 |
| $C_{11+}$ Aromatics | 0.2 | 0.04 | 0.04 | Trace | Trace |
| Wt. % Xylene | | | | | |
| P-xylene | 24.1 | 24.7 | 24.6 | 23.4 | 23.3 |
| O-xylene | 19.3 | 17.6 | 17.2 | 14.0 | 12.9 |
| M-xylene | 56.6 | 57.7 | 58.1 | 62.5 | 63.8 |
| EB Conv. Wt. % | 24.4 | 21.5 | 15.7 | 9.3 | 8.7 |
| Xylene Loss Wt. % | 0.5 | +0.3 | 0.1 | 0.1 | +0.1 |

Although p-xylene approach to equilibrium remains fairly constant over the twelve day run, the yield of o-xylene drops severely and the conversion of EB drops by over 64% at constant temperature. It is to be expected that as pressure is further reduced the efficiency of the operation will be further impaired as compared with high pressure vapor phase isomerization over zeolite ZSM-5.

Typical process conditions, performance parameters and yields for the low pressure xylene isomerization process of this invention and conventional silica alumina operation are compared below.

| Process Conditions | Si/Al | 65% ZSM-5 35% $Al_2O_3$ |
|---|---|---|
| Pressure, psig | 25 | 25 |
| Space Velocity, WHSV | 1 | 5 |
| Temperature, ° F. | 800–900 | 550–750 |
| Performance | | |
| Cycle Length, days | 2–4 | >180 |
| P-xylene Equilibrium Approach, % | 80 | 100 |
| Ultimate Yield, Wt. % | | |
| $C_5^-$ | 2.1 | 0.2 |
| Benzene & Toluene | 9.8 | 2.7 |
| Para-xylene | 75.7 | 93.2 |
| $C_9^+$ Aromatics | 12.4 | 3.9 |
| | 100.0 | 100.0 |

The efficiency of the ZSM-5 catalyst for low pressure xylene isomerization results in less severe operating conditions, significantly longer cycles between regenerations, increased equilibrium approach, and higher yield of para-xylene. These advantages result in higher product value, higher throughput, and lower utility requirements.

In addition, as indicated above, the present invention provides high rates for conversion of EB at very low xylene loss by conversion to other products as contrasted with high loss of xylenes when EB is converted from a mixture with xylenes over silica/alumina. As expected, both catalysts show a parallel of activities for conversion of EB and xylenes, however, the ratio between the two activities is very different. To maintain operation at acceptable xylene recovery of about 75% with silica/alumina catalyst without excessive EB build up, it is necessary to subject the feed material to expensive distillation for reduction of EB to 5% or less. With zeolite ZSM-5 as the catalyst, high EB content of feed can be converted while operating at conditions to recover more than 90% of the xylenes as p-xylene.

The process of this invention was conducted in two pilot plant runs. The unit used has three semi-adiabatic reactors in series, but only one reactor was charged with catalyst (40 cc fill). One run evaluated the operation over a catalyst of small crystal (0.05 micron) HZSM-5 in 35% by weight of alumina. A large crystal (0.5 micron) HZSM-5 catalyst was used in the second run. Experimental conditions are summarized in Table 2.

Feedstock compositions are shown in Table 3. Except for the first charge to run 1, the xylene distribution is below equilibrium for para-xylene and above equilibrium for the ortho and meta isomers. This distribution simulates a commercial plant where p-xylene is the only xylene produced from the loop. Ethylbenzene concentration varied from 6.9 to 20.5 wt %. The lower value represents the case where some ethylbenzene is removed prior to the loop via distillation. The higher concentrations simulate the case where all of the ethylbenzene normally in the $C_8$ aromatic fraction from reforming is included in the loop feed.

All liquid feed was pumped over a bed of activated alumina before it was charged to the unit. This step removes oxygenated hydrocarbons (e.g., peroxides). Blended laboratory stocks contain trace quantities of these components because feed preparation necessitates exposure to the atmosphere. This is generally not the case for commercial plants, so the alumina pre-bed would not be required.

A small amount of nitrogen (equivalent to about 0.2 mols/mol HC) was fed to the unit to maintain pressure. During all of the first run and the first 48 days of the second run, the nitrogen was combined with the liquid feed and passed over the catalyst. After this point, the nitrogen was fed to the back of the unit (before the back pressure control valve) in order to bypass the catalyst bed. Without this purge stream, the small gas production typical of the new process makes it difficult to operate the unit at constant pressure and obtain representative gas samples.

TABLE 2

| Summary of Experimental Conditions | | |
|---|---|---|
| Run No. | 1 | 2 |
| Process Conditions | | |
| Pressure, psig | 25 | 25 |
| Space Velocity, WHSV | 5–7.5 | 5–8.5 |
| Temperature, ° F. | 550–630 | 550–720 |
| $H_2$/HC. mols/mol feed | | |
| Ethylbenzene Conversion, % | 7.5–30 | 25 |
| Feed Ethylbenzene, Wt % | 6.9–15.1 | 20.2–20.5 |
| Time On-Stream, Days | 73 | 180 |
| Status | Terminated | Continuing |

TABLE 3

| | Feedstock Composition | | | | | | |
|---|---|---|---|---|---|---|---|
| Run No. | 1 | | | 2 | | | |
| Charge Code | A | B | C | D | E | F | G |
| Time On-Stream, Days | 0–16 | 17–52 | 53–73 | 0–32 | 33–48 | 49–102 | 103– |
| Composition, Wt. % | | | | | | | |
| $C_6$ + PON* | 0.3 | 0.0 | 0.1 | 0.0 | 0.0 | 0.0 | 0.0 |
| Benzene | 0.0 | 0.0 | 0.0 | 0.0 | 0.0 | 0.0 | 0.0 |
| Toluene | 0.9 | 0.1 | 0.3 | 0.0 | 0.1 | 0.1 | 0.0 |
| Ethylbenzene | 6.9 | 15.1 | 14.1 | 20.3 | 20.5 | 20.5 | 20.2 |
| Xylenes - para | 10.3 | 9.1 | 9.2 | 8.4 | 8.6 | 8.7 | 9.0 |
| - meta | 63.0 | 54.6 | 54.9 | 50.6 | 50.8 | 50.7 | 50.8 |
| - ortho | 18.6 | 21.1 | 21.0 | 20.4 | 20.0 | 20.0 | 20.0 |
| $C_9^+$ Aromatics | 0.0 | 0.0 | 0.4 | 0.3 | 0.0 | 0.0 | 0.0 |
| | 100.0 | 100.0 | 100.0 | 100.0 | 100.0 | 100.0 | 100.0 |
| Xylene Fraction, Wt. % | | | | | | | |
| Para-xylene | 11.2 | 10.7 | 10.8 | 10.6 | 10.8 | 10.9 | 11.3 |
| Meta-xylene | 68.6 | 64.4 | 64.5 | 63.7 | 64.0 | 63.9 | 63.7 |
| Ortho-xylene | 20.2 | 24.9 | 24.7 | 25.7 | 25.2 | 25.2 | 25.0 |
| | 100.0 | 100.0 | 100.0 | 100.0 | 100.0 | 100.0 | 100.0 |

*Paraffins, olefins, naphthenes

The process has been evaluated for more than six months over the catalyst of Run 2 at 25 psig, 25% EB conversion and 5–8.5 WHSV, based on total of composite corresponding to 7.7–13 based on zeolite. The catalyst lost activity for EB conversion equivalent to 20° F. per month at 5 WHSV and 35° F. per month at 8.5 WHSV.

Typical yields for the low EB feedstock are shown in Table 4. Similar data for the high EB feedstock are reported in Table 5.

Typically, the process of this invention is conducted by continuous charge of a $C_8$ aromatics mixture at temperatures ranging between 500° F and 750° F for a period of more than 30 days, preferably at least 100 days. It is shown that continuous runs of six months or more are possible. As activity of the catalyst declines, the temperature of reaction is increased within the said range. Conveniently, the activity is observed as conversion of EB and the temperature is increased over the course of the run to the degree which maintains the conversion of EB substantially constant. Ordinarily, the increase in temperature is step-wise, being increased at intervals of a few days.

TABLE 4

| Yield from Low EB Feed | |
|---|---|
| Pressure, psig | 25 |
| WHSV | 5 |
| Temperature, ° F. | 600 |
| $H_2$/HC, Molar | 0 |
| Ethylbenzene Conversion | 24.6 |
| Wt. % | |
| $C_5^-$ | 0.0 |
| $C_6^+$ PON* | 0.3 |
| Benzene | 0.7 |
| Toluene | 1.6 |
| Ethylbenzene | 5.2 |
| Xylenes - para | 21.9 |

TABLE 4-continued

| Yield from Low EB Feed | |
|---|---|
| - meta | 48.9 |
| - ortho | 19.5 |
| C$_9^+$ Aromatics | 1.9 |
| | 100.0 |

*Paraffins, olefins & naphthenes

TABLE 5

| Yield From High EB Feed | |
|---|---|
| Pressure, psig | 25 |
| WHSV | 5 |
| Temperature, °F | 600 |
| H$_2$/HC, Molar | 0 |
| Ethylbenzene Conversion | 23.6 |
| C$_5^-$ | 0.1 |
| Benzene | 1.9 |
| Toluene | 0.5 |
| Ethylbenzene | 15.5 |
| Xylenes - para | 19.0 |
| - meta | 42.2 |
| - ortho | 17.2 |
| C$_9^+$ Aromatics | 3.6 |
| | 100.0 |

From the results so obtained experimentally, the ultimate yields from operation in a loop of the type shown in the drawing may be calculated. So calculated values are shown in Table 6.

TABLE 6

Comparison of Ultimate Yield for HZSM-5 with Silica/Alumina Operation

| | | Loop Product | | |
|---|---|---|---|---|
| | | Silica/Alumina | HZSM-5 | |
| Ethylbenzene Conversion, % | Loop Feed | — | 25 | 7.5 |
| Yield, Wt. % | | | | |
| Gas | | 2.1 | 0.2 | 0.2 |
| Benzene & Toluene | | 9.8 | 5.1 | 2.7 |
| Ethylbenzene | 5.0 | — | — | — |
| Xylenes - para | 24.4 | 75.7 | 87.3 | 93.2 |
| - meta | 47.4 | — | — | — |
| - ortho | 23.2 | — | — | — |
| C$_9^+$ | — | 12.4 | 7.4 | 3.9 |
| | 100.0 | 100.0 | 100.0 | 100.0 |

We claim:

1. In a process for manufacture of p-xylene from a mixture of eight carbon atom aromatic hydrocarbons containing ethyl benzene and the three xylene isomers by adding said mixture to a cyclic stream of hydrocarbons in a processing loop which includes a recovery stage for removal of p-xylene from the stream followed in turn by an isomerization stage for low pressure catalytic isomerization of xylenes, a distillation stage for removal of compounds boiling above and below the boiling range of eight carbon atom aromatic compounds and return of the eight carbon atom hydrocarbon stream derived from said distillation to said recovery stage;

the improvement resulting in prolonged on-stream periods of the process between catalyst regenerations which comprises adding said mixture to said loop substantially free of peroxide, conducting the said isomerization stage in the presence of a catalyst having activity for isomerization of xylenes and for conversion of ethyl benzene to higher and-/or lower boiling hydrocarbons consisting essentially of an aluminosilicate crystalline zeolite having a silica to alumina ratio of at least 12 and a constraint index of 1 to 12 at a partial pressure of said eight carbon atom alkyl aromatic compounds below about 100 pounds per square inch, a temperature range between about 500° F. and about 800° F. and a space velocity of 3 to 13 pounds of said eight carbon atom aromatic compounds per pound of said zeolite per hour, initiating the isomerization at a temperature in the lower portion of said range at conditions of temperature, pressure and space velocity to convert ethyl benzene at a rate to maintain ethyl benzene concentration in the loop approximately equal to that in said mixture, observing ethyl benzene in said loop and increasing temperature in said isomerization stage within said range during the process to maintain ethyl benzene conversion at a rate to maintain ethyl benzene concentration in the loop approximately equal to that in said mixture.

2. A process according to claim 1 wherein said silica/alumina ratio is at least 30.

3. A process according to claim 1 wherein said zeolite is ZSM-5.

4. A process according to claim 1 wherein said zeolite is in the hydrogen form.

5. A process according to claim 1 wherein said zeolite is combined with an inert matrix.

6. A process according to claim 3 wherein said zeolite is HZSM-5.

7. A process according to claim 3 wherein said zeolite is combined with an inert matrix.

8. A process according to claim 7 wherein said matrix is alumina.

* * * * *